US005447530A

United States Patent [19]

Guibert et al.

[11] Patent Number: 5,447,530

[45] Date of Patent: Sep. 5, 1995

[54] PERIODIC PULSED HEAT TECHNIQUE FOR INDUCING ANALGESIC EFFECTS

[76] Inventors: Raul Guibert; Bettina Guibert, both of 750 S. Bundy Dr., Brentwood, Calif. 90049

[21] Appl. No.: 219,084

[22] Filed: Mar. 28, 1994

[51] Int. Cl.[6] .......... A61F 7/00

[52] U.S. Cl. .......... 607/107

[58] Field of Search .......... 607/96, 104, 107–108

[56] References Cited

U.S. PATENT DOCUMENTS

| | | | |
|---|---|---|---|
| 4,398,535 | 8/1983 | Guibert | 607/107 |
| 4,595,008 | 6/1986 | Guibert | 607/107 |
| 4,628,931 | 12/1986 | Barrett | 607/107 X |
| 4,667,658 | 5/1987 | Guibert | 607/107 X |
| 5,209,227 | 5/1993 | Deutsch | 607/104 |

*Primary Examiner*—Angela D. Sykes

*Attorney, Agent, or Firm*—Michael Ebert

[57] ABSTRACT

A technique for inducing analgesic effects to relieve pain in a living organism whose central nervous system is associated with thermal receptors in the skin that sense heat and transmit signals through afferent fibers reflecting the intensity of the heat and its duration to the brain via the spinal cord. Applied to an area of the skin for a predetermined period is an air stream whose temperature is periodically elevated to create high-temperature pulses separated by lower temperature intervals whereby as a result of heat transfer from the skin area to tissue underlying the skin, the temperature at the surface of the skin is at a tolerable level. The signals transmitted to the brain during this period that reflect the sensed high temperature pulses stimulate the brain into producing endorphins having analgesic effects on the organism and relieving pain.

7 Claims, No Drawings

PERIODIC PULSED HEAT TECHNIQUE FOR INDUCING ANALGESIC EFFECTS

BACKGROUND OF INVENTION

1. Field of Invention

This invention relates generally to analgesics to relieve pain in living organisms both human and animal, and more particularly to a periodic pulsed heat technique which induces analgesic effects in the organisms without the use of drugs.

2. Status of Prior Art

The term analgesic refers to a drug whose chemical structure and physiological effects are such that when the drug is administered, it then acts to relieve pain. To qualify as an analgesic, the drug must reduce or abolish pain without, however, impairing consciousness, causing mental confusion or otherwise deranging the nervous system. Thus a drug which renders the patient unconscious is not an analgesic, but an anesthetic, even though it abolishes pain.

One well-known class of analgesics are the narcotic alkaloids. The oldest and best known are opium and morphine, its most active alkaloid. Also derived from opium is codeine. A person who takes opium or its derivatives for a prolonged period needs and tolerates larger and larger doses to obtain the desired effect, and therefore, becomes habituated. Should the use of the drug be then stopped, highly disagreeable withdrawal symptoms are experienced. Narcotic alkaloids are all potentially addictive, and an addict will often go to great lengths to obtain the narcotic to avoid withdrawal symptoms. Among non-narcotic analgesic drugs are the salicylates, such as aspirin. But these are far less effective in reducing pain than morphine and synthetic opiods.

Endorphins are manufactured within the central nervous system and share with narcotic alkaloids the ability to relieve pain. Endorphins function as neuromodulators in a system descending from the brain through the spinal cord which counteract painful impulses coming from the periphery toward the brain.

The term "endorphin" is an elision of ENDOgenous and moRPHINe. "Endogenous" means produced within the body, as distinguished from "exogenous" which means produced outside of the body. The term endorphin is now generic to a family of endogenous opiates that include leucine enkephalin, and alpha, beta, gamma and delta endorphin; as well as a growing number of synthetic compounds. The reason narcotic analgesic drugs are effective is that they mimic the actions of natural endorphins by occupying stereospecific opiate receptors in the brain, the spinal cord and the gut, normally occupied by endorphins.

For purposes of classification, drugs which have analgesic properties fall into the exogenous class, while internallygenerated endorphins fall into the endogenous class of analgesics. The problem with exogenous analgesics is that these drugs have adverse side effects, especially if used to excess. Indeed, the more powerful the drug, the greater its undesirable side effects. Yet these drugs are often prescribed, for internally-produced endorphins are inadequate to relieve severely painful conditions. The human brain which governs the generation of endorphins is dedicated to the survival of the body it occupies, and the brain, therefore, manipulates the production of endorphins toward this end. Thus when a soldier in battle is slashed by a bayonet, though bleeding profusely, he then experiences little pain, for the pain sensation is blocked by endorphins. This makes it possible for the soldier to continue fighting, for it is only later that intense and disabling pain is experienced.

However, pain control is but one function of the central nervous system composed of the brain and the spinal cord which together control and correlate body actions and reactions. The central nervous system operates in conjunction with a network of peripheral nerves whose sensory or afferent nerves convey signals via the spinal cord to the brain. These signals stimulate the brain to act in a manner appropriate to the information it receives from the internal sensors.

Every sensation experienced by a living organism depends on impulses excited by stimulation of receptors. Thus heat is detected by heat-sensitive receptors in the skin, the electrochemical impulses or signals emitted by the receptors being delivered by afferent nerve fibers in the peripheral nervous system via the spinal cord to the brain. Other receptors in the skin and those distributed throughout tissue underlying the skin and elsewhere in the body, sense touch and other stimuli, but these are not the concern of the present invention whose interest is limited to thermal receptors and the signals produced thereby.

When in the example given above, our soldier is slashed, the nervous reaction not only stimulates the brain into producing endorphins to reduce the sensation of pain, but also to cause swelling near the site of the wound. This swelling clears the way for emergency measures which include phagocytes produced by the immune system that pour into the wounded region to consume bacteria, viruses and dead cells, and thereby promote the healing process.

The thermal receptors in the skin that signal the brain are responsive to the temperature of the sensed heat regardless of the extent of tissue damage produced by the heat to which the human organism is exposed. Thus if the heat to which the body is exposed produces a severe burn and the receptors then detect a temperature of say 140° F., the signals produced by the receptors will be the same as when pulsed-heat is applied to the body which results in a temperature of 140° F., yet does not give rise to a burn. In either case, the brain receives the same stimuli from the sensors, and the brain will take the same emergency measures, including the production of endorphins to reduce the sensation of pain.

In a pulsed-heat technique in accordance with the invention, in order to produce pulsed-heat having an analgesic effect comparable to that produced by exogenous drug analgesics, but without adverse side effects, use is preferably made of a pulsed-heat applicator of the type disclosed in our 1992 U.S. Pat. No. 5,107,832 entitled "Universal Thermotherapy Technique."

The applicator disclosed in our patent includes a casing dome whose open base is maintained in spaced relation to a skin area of a patient to define an air flow zone therebetween. Coaxially mounted at an intermediate position within the dome is a motor-driven fan which creates a negative pressure region in the dome above the fan and a positive pressure region therebelow, whereby air drawn from the negative pressure region is propelled into the positive pressure region from which it is discharged into the air flow zone. From this zone, the air is returned to the negative pressure region, thereby creating a circulatory flow loop minimizing the discharge of air into the atmosphere outside the flow zone.

Mounted coaxially within the dome in the negative pressure region is an electric heater ring formed by a helical resistance coil. When the heater ring is energized, the air circulating in the loop passes through the coil and is raised in temperature to a level that is a function of fan velocity, the higher the velocity the lower the temperature level. An electronic control unit associated with the fan motor acts to periodically change the fan velocity from a predetermined high value at which the resultant temperature level of the air in the flow zone is then at a base level above ambient but somewhat below the sensitivity threshold of the patient being treated, to a predetermined low velocity value at which the resultant temperature level is reaised above the base level to create high temperature heat pulses whose peaks are well above the sensitivity threshold.

A pulsed-heat applicator of the type disclosed in our prior patent is adapted to apply heat to a problem region underlying the skin surface without however raising the temperature at the surface of the skin to a level that cannot be tolerated by the patient. The difficulty heretofore experienced in effectively applying heat to a patient is that when the heat is transferred inwardly through living tissue to the problem region, then if the heat applied to the skin surface for this purpose is within a tolerable temperature range and does not burn the skin, not enough heat energy is transferred to the site being treated to afford beneficial therapeutic effects. This drawback is overcome by the applicator disclosed in our prior patent in which the applied heat is in the form of periodic high-temperature pulses.

The duty cycle of these pulses is such as to allow for internal heat transfer to take place in the tissue below the exposed skin area of the patient in the intervals between pulses to an extent preventing an excessive rise in temperature at the skin surface whereby the patient gains the benefit of high heat energy treatment without discomfort or injury.

The concern of the present invention is not with the application of elevated heat to an internal problem region of the body, but with the application of heat to a skin area of the body to excite the thermal receptors in the skin to produce signals stimulating the brain to produce endorphins having analgesic effects. While the application of pulsed heat to the skin will inevitably result in the transfer of heat to regions underlying the skin, the extent to which these region is heated is an incidental effect. In the present invention, no more heat is applied to the skin than is necessary to induce analgesic effects.

SUMMARY OF INVENTION

The main object of this invention is to provide a technique for inducing analgesic effects in a living organism without the use of drugs.

More particularly, an object of this invention is to provide a technique in which applied to a heat-sensitive area of the skin is an air stream whose temperature is periodically elevated whereby the resultant periodic pulsed heat applied to this area and sensed by thermal receptors in the skin causes the receptors to send signals to the brain stimulating the brain to produce endorphins having an analgesic effect on the organism.

Briefly stated these objects can be obtained by a technique for inducing analgesic effects to relieve pain in a living organism whose central nervous system is associated with thermal receptors in the skin that sense heat and transmit signals through afferent fibers reflecting the intensity of the heat and its duration to the brain via the spinal cord. Applied to an area of the skin for a predetermined period is an air stream whose temperature is periodically elevated to create high-temperature pulses separated by lower temperature intervals whereby as a result of heat transfer from the skin area to tissue underlying the skin, the temperature at the surface of the skin is at a tolerable level. The signals transmitted to the brain during this period that reflect the sensed high temperature pulses stimulate the brain into producing endorphins having analgesic effects on the organism and relieving pain.

DESCRIPTION OF INVENTION

In a technique in accordance with the invention for producing analgesic effects without the use of drugs, periodic pulsed heat is applied to a skin area of a person or animal suffering from pain. The pulsed heat applicator may be of the type disclosed in our prior U.S. Pat. No. 5,167,832, in the Guibert U.S. Pat. No. 4,667,658, or by any other means capable of producing periodic pulsed heat in a form producing analgesic effects.

The stream of air providing periodic pulsed heat is applied to a skin area of the living organism being treated which has a high sensitivity to heat. We find that a skin area in the lumbar region of the body has this high sensitivity, for it is adjacent to the spinal cord and the thermal receptors in this skin area are closely linked by afferent nerve fibers in the peripheral nervous system with the spinal cord which conveys the signals yielded by the receptors to the brain of the central nervous system. It is to be understood, however, that any skin area of the body which is similarly heat-sensitive can be exposed to the periodic pulsed heat to induce analgesic effects.

The air stream produced by the applicator and directed toward the selected skin area, has a temperature which is periodically elevated to create high-temperature pulses separated by lower temperature intervals. The relationship of these pulses to the intervals must be such as to excite the thermal receptors to induce an analgesic effect, rather than to elevate, as in our prior patents, the temperature of a problem region underlying the skin surface so as to obtain therapeutic effects, such as the relaxation of constricted muscles.

We have found that excitation of the thermal receptors in the skin is best carried out by periodic high heat energy pulses having a very brief duration such as 50 milliseconds, a peak temperature of 55° to 90° C., and a relatively prolonged interval between successive pulses, such as 5 seconds. The temperature of the air stream in these intervals is above normal body temperature, but much lower than the pulsed heat peak temperature. While the peak temperature level is such that if applied continuously to the skin, the skin would be scorched, because of the brevity of these pulses and the long interval therebetween, no damage is sustained by the skin, even when the periodic pulsed heat air stream is applied to the skin for 30 minutes or more.

However, the high peak temperature of the pulses excite the thermal receptors in the skin, the receptors drawing no distinction between a very high temperature capable of scorching the skin when applied continuously, and the same temperature applied in the form of brief pulses with a long interval between pulses. Since the receptors in response to periodic pulsed heat, yield a pulsatory signal rather than a steady state signal, this pulsatory signal has a far greater effect on the brain to simulate it to produce endorphins, than a steady state signal, this pulsatory signal has a far greater effect on the brain to simulate it to produce endorphins, than a steady state signal for the brain has a higher degree of alertness to blinking or pulsatory signals than to steady signals. Thus a blinking strobe light excites a far stronger reaction than a steady, high-intensity light.

When the thermal receptors are excited by the periodic pulsed heat for several minutes, say thirty minutes, the electrochemical impulses or signals yielded by the receptors which reflect the intensity of the heat and its pulse duration are conveyed through the afferent nerves of the peripheral nervous system via the spinal cord to the brain of the central nervous system. The signals transmitted to the brain during the period in which the pulsed-heat air stream is applied to the skin, act to stimulate the brain into producing endorphins having a powerful analgesic effect on the organisms being treated and relieve pain. Indeed, we have found in treating many patients, that the relief from pain they experienced was so great as to cause them to fall asleep.

In order to qualitatively test the effectiveness of an analgesic, it is the known practice to use naloxone (Narcon) for this purpose, for the action of this drug is to reverse the effects of opiods. One can, therefore, use naloxone to determine the presence of endorphins by measuring certain clinical signs known to be affected by opiods.

Clinical tests were run on eight subjects, each of whom in a prone position was subjected to periodic pulsed heat applied to the skin surface of the lumbar region for 30 minutes. During this treatment, the vital signs and the alertness level of each subject was continuously monitored. At the end of treatment, naloxone was administered to the subject.

The results of these tests indicated that each subject treated with pulsed heat exhibited significant reductions in vital signs (mean arterial blood pressure, respiratory rate, pulse rate, etc.) as well as in alertness level. Following the injection of naloxone, each subject exhibited a significant return to the baseline of all monitored parameters.

These tests and many others conducted by the applicants support the conclusion that periodic pulsed heat applied to skin area of a subject activates his or her endogenous opiod-mediated analgesic system. The technique provides a highly effective method of producing analgesia in a home or in a clinical setting without the use of analgesic drugs, and without their adverse side effects.

The analgesic effect generated by the application of periodic pulsed heat to a skin area of a subject is progressively produced; hence the pulsed heat is applied without interruption for a period, such as 20 to 30 minutes or more, until the subject experiences adequate relief from pain. But once the production of endorphins is stimulated during this period in a volume sufficient to relieve pain in the subject being treated, the endorphins which then occupy the opiate receptors in the brain remain effective for a prolonged period after heat treatment.

In practice, it is desireable, before applying pulsed heat to the skin area, to first coat this area with vaseline or other suitable skin cream to prevent the skin from drying out.

The film of vaseline coating of the skin area displaces the static air film that normally adheres to the skin. Because this coating has a far greater thermal conductivity than air, it promotes a more rapid response by the thermal receptors in the skin. And it is important to bear in mind that when the brain is stimulated to produce endorphins, at the same time the immune system is activated into producing healing agents.

While there has been described an analgesic technique in accordance with the invention, it will be appreciated that many changes may be made therein without departing from the spirit of the invention.

We claim:

1. A technique for inducing an analgesic effect to relieve pain in a living organism whose skin has thermal receptors therein coupled by afferent nerves to the brain of the central nervous system via the spinal cord, said technique comprising the steps of:

A. applying to a selected skin area of the organism thermal energy whose temperature is periodically elevated to create high-temperature pulses, each having a duration of about 50 milliseconds, separated by relatively low temperature intervals, each having a duration in the seconds range, whereby the receptors in the skin yield signals reflecting the heat intensity and duration of these pulses which are conveyed by the nerves to the brain; and B. continuing to apply this thermal energy to the skin area for a period sufficient to cause the signals applied to the brain to stimulate the brain into producing endorphins having an analgesic effect on the organism to relieve pain.

2. A technique as set forth in claim 1, in which the thermal energy is applied by an air stream which flows along the surface of the skin area.

3. A technique as set forth in claim 1, in which the relative duration of the pulses and the intervals therebetween, and the relative temperatures of the pulses and intervals are such that the skin temperature is at a tolerable level.

4. A technique as set forth in claim 1, in which the peak temperature of the pulses exceeds 50° C.

5. A technique as set forth in claim 1, in which the selected skin area is adjacent the spinal cord.

6. A technique as set forth in claim 1, in which the selected skin area is in the lumbar region.

7. A technique as set forth in claim 1, in which the skin area is coated with a cream serving to prevent the area from drying out.

* * * * *